United States Patent
Barak

(10) Patent No.: US 7,774,883 B2
(45) Date of Patent: Aug. 17, 2010

(54) ORTHOPEDIC INSOLES FOR PROTECTING THE METATARSAL HEADS OF THE FOREFOOT

(76) Inventor: Yahoshua Barak, 49 Krauze, Holon (IL) 58350

(*) Notice: Subject to any disclaimer, the term of this patent is extended or adjusted under 35 U.S.C. 154(b) by 452 days.

(21) Appl. No.: 10/595,170

(22) PCT Filed: Sep. 9, 2004

(86) PCT No.: PCT/IL2004/000822

§ 371 (c)(1),
(2), (4) Date: Mar. 16, 2006

(87) PCT Pub. No.: WO2005/025356

PCT Pub. Date: Mar. 24, 2005

(65) Prior Publication Data

US 2007/0094815 A1    May 3, 2007

Related U.S. Application Data

(60) Provisional application No. 60/502,943, filed on Sep. 16, 2003.

(51) Int. Cl.
*A43B 7/14* (2006.01)
(52) U.S. Cl. .................... 12/142 N; 12/146 M
(58) Field of Classification Search ........... 12/142 N, 12/146 M, 146 B, 142 R; 36/43, 44, 174, 36/180
See application file for complete search history.

(56) References Cited

U.S. PATENT DOCUMENTS

| 1,901,353 | A | * | 3/1933 | Mitchie | 12/146 R |
| 4,520,581 | A | * | 6/1985 | Irwin et al. | 12/142 N |
| 4,702,255 | A | | 10/1987 | Schenkl | |
| 6,745,501 | B2 | * | 6/2004 | Brown | 36/174 |
| 7,153,457 | B2 | * | 12/2006 | Shor | 12/142 N |
| 7,206,718 | B2 | * | 4/2007 | Cavanagh et al. | 702/155 |
| 7,380,352 | B2 | | 6/2008 | Seiter | |

FOREIGN PATENT DOCUMENTS

| EP | 0495152 | 5/1991 |
| EP | 0495152 | 7/1992 |
| RU | 2182808 | 5/2002 |
| WO | WO03/090573 | 11/2003 |
| WO | WO03090573 | 11/2003 |

OTHER PUBLICATIONS

International Preliminary Report on Patentability for PCT/IL2004/000822 filed Sep. 9, 2004.
Written Opinion of the International Searching Authority for PCT/IL2004/000822 filed Sep. 9, 2004.
International Search Report for PCT/IL2004/000822 filed Sep. 9, 2004.

* cited by examiner

*Primary Examiner*—Ted Kavanaugh
(74) *Attorney, Agent, or Firm*—Martin Fleit; Paul D. Bianco; Fleit Gibbons Gutman Bongini & Bianco PL

(57) ABSTRACT

A specially designed insert for orthopedic insoles and a process for manufacturing said insole, the use of which prevents the foot from bending excessively at the metatarsal joints, thereby protecting the skin in the area of the metatarsal heads of the forefoot on the bottom of the foot and preventing that skin from stretching, cracking or being otherwise damaged.

4 Claims, 10 Drawing Sheets

Fig 3
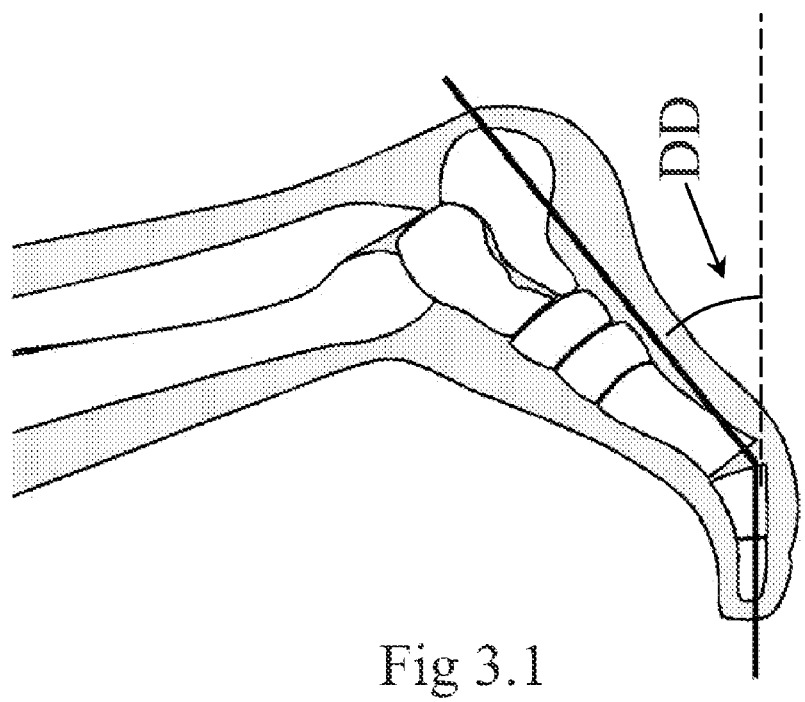
Fig 3.1
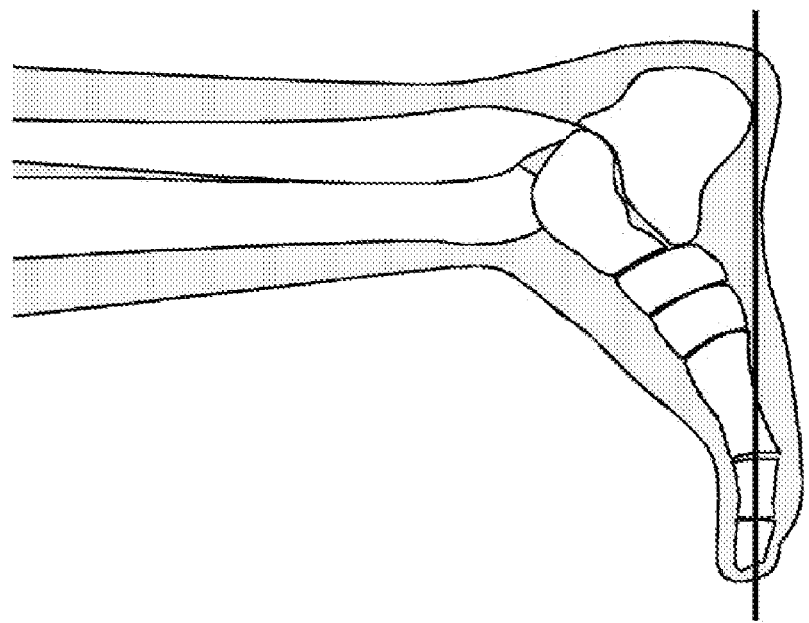

ORTHOPEDIC INSOLES FOR PROTECTING THE METATARSAL HEADS OF THE FOREFOOT

This Application is the National Stage of International Application No. PCT/IL 04/000822 filed Sep. 9, 2003, which claims the benefit of U.S. Provisional Application No. 60/502,943 filed Sep. 16, 2003.

FIELD OF INVENTION

This invention relates generally to medical devices for treating diabetic side effects and specifically to protective orthopedic insoles.

BACKGROUND OF THE INVENTION

While walking or running, the feet are engaged in the continuous movement of taking repeated steps. These steps can be broken down into different actions. Each step begins when the heel of one foot strikes the ground. The foot continues moving forward in a rolling fashion through to the toes. As seen in FIG. 1, the toes reach the ground during this phase of the step while, simultaneously, the heel begins to rise (points A and B). Once the toes touch the ground, the foot must carry through the step by further raising the heel. This motion is represented in FIG. 2. Point C of FIG. 2 represents the height the heel must reach in order to complete a step. Raising the heel during this stage of the step causes the foot to bend in the area of the five metatarsal Metatarsal-phalangeal joints, also referred to as the five metatarsal heads of the forefoot (see FIG. 5), and the skin in the area of the forefoot stretches. FIG. 3, angle DD shows the angle of the bend at the five metatarsal phalangeal joints. The bending occurrence in the area of the five Metatarsal-phalangeal joints of the forefoot is easily discernable in shoes that often have a crease in the area where this bending occurs, as shown in point D of FIG. 2. Once the heel reaches the necessary height, the foot breaks contact with the ground and returns to a straight position while the second foot begins its step, repeating the process.

Raising the heel in the course of taking a step causes the foot to bend in the area of the five metatarsal heads of the forefoot, necessarily stretching the skin in this area and possibly causing friction. People who have diabetes and other diseases that affect the feet face greater risks; bending the skin in the area of five metatarsal heads can crack the skin, which may lead to severe and painful wounds.

For people so afflicted, even minor injuries can take long periods to heal, and can grow worse over time if not treated properly. Therefore, any condition that may potentially damage the skin must be avoided. However, existing shoes and insoles do not provide the room necessary to complete a step with significantly reduced bending of the foot. This means the skin in the area of the five metatarsal heads of the forefoot is constantly exposed to potential damage. Currently, no preventive actions or devices exist to correct such limitations in existing shoes and insoles and to protect the skin in the area of the metatarsal heads from bending, stretching, and cracking.

SUMMARY OF INVENTION

The innovation presented here is a process for creating a uniquely formed orthopedic insole by adding a specially designed insert to the casting used to create the insoles. This new insole provides ample room for the foot to complete a step while preventing the problems associated with the bending motion described above by limiting said motion.

These orthopedic insoles, created by utilizing the proposed method of a specially designed insert at the area of the five metatarsal heads of the forefoot, will significantly decrease or prevent the stretching and cracking of the skin in the area of the five metatarsal heads of the forefoot.

BRIEF DESCRIPTION OF DRAWINGS

FIG. 3 and FIG. 3.1 Show the positions of the feet during the step phases.

DESCRIPTION OF THE PREFERRED EMBODIMENT

This innovation proposes to create an insole that provides ample room for walking, while significantly alleviating the problems associated with the bending motion described above. In order to create this new insole, a specially designed insert is added to the casting used to create the insoles. The proposed insert can be created from various types of materials.

Figure 4:
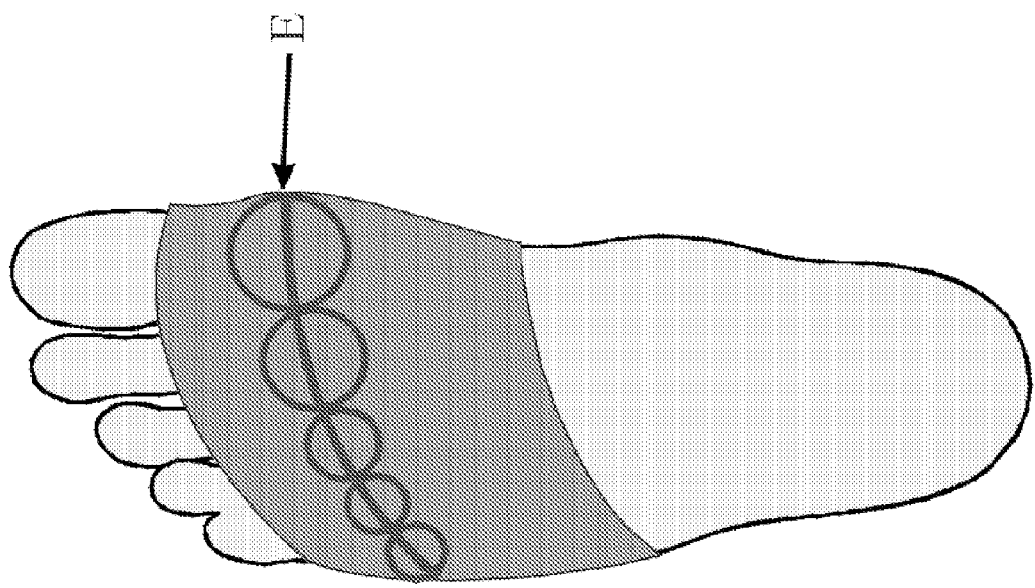
FIG. 4 highlights the location of the five metatarsal heads of the forefront on the bottom of the foot.
Figure 5:
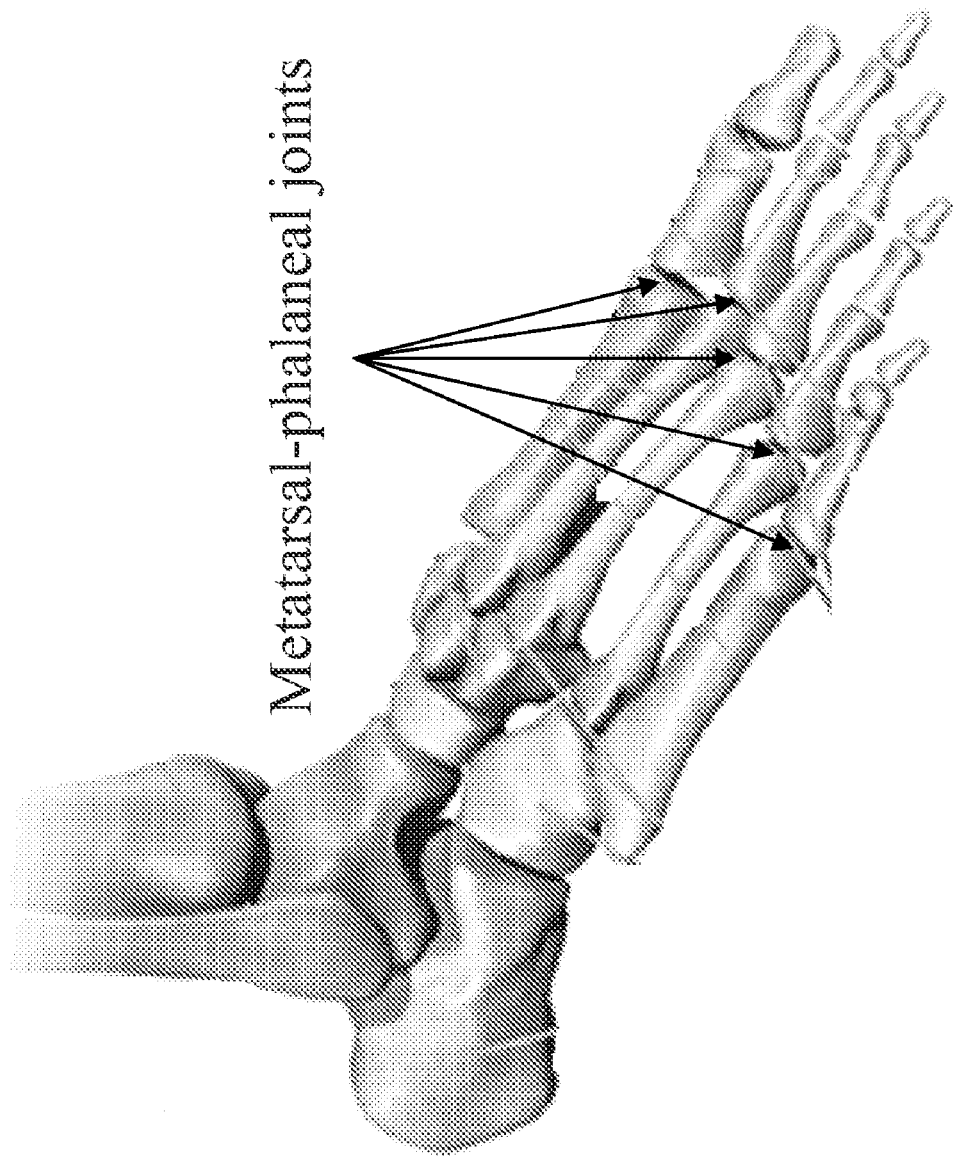
FIG. 5 shows the locations the five metatarsal heads of the forefront of the foot.

This application relates to the area of the five metatarsal heads of the forefoot, on the bottom of the foot, seen in FIG. 4, Point E, and in FIG. 5 in the area labeled "Metatarsal-phalangeal joints" (hereinafter "the Metatarsal Heads"). "Cracking" relates to diabetics, who suffer from this occurrence on their feet.

The Innovation

This innovation proposes to create an insole with ample room for walking, while preventing the problems associated with the bending motion described above. In order to create this new insole, a specially designed insert is added to the casting used to create the insoles.

The first step in creating the new orthopedic insoles is to cast the patient's feet in plaster. Using the individualized plaster casting, any of various methods are incorporated in forming the insole.

Next, the specially designed insert, typically between 3 mm and 35 mm, will be measured and created specifically for each patient. The thickness of the insert is dependent on the patient's foot structure. The insert covers the area of the five metatarsal heads of the forefoot, and ensures that the insole will be created with enough space for the foot to complete a step without significantly bending the area of the five metatarsal heads of the forefoot. The insert can be created from various types of materials.

Figure 6:
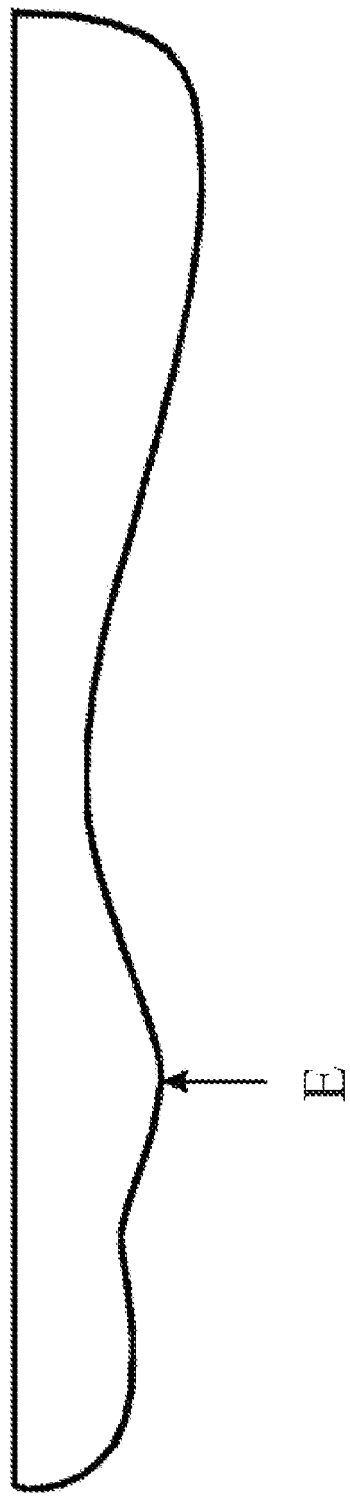
FIG. 6 represents a prior art plaster casting of the foot.

FIG. 6 represents a typical plaster casting of a foot used for creating currently available insoles. As shown in the Fig, the prior art insole touches the ground at the area of the five metatarsal heads of the forefoot, at point E.

Figure 7:
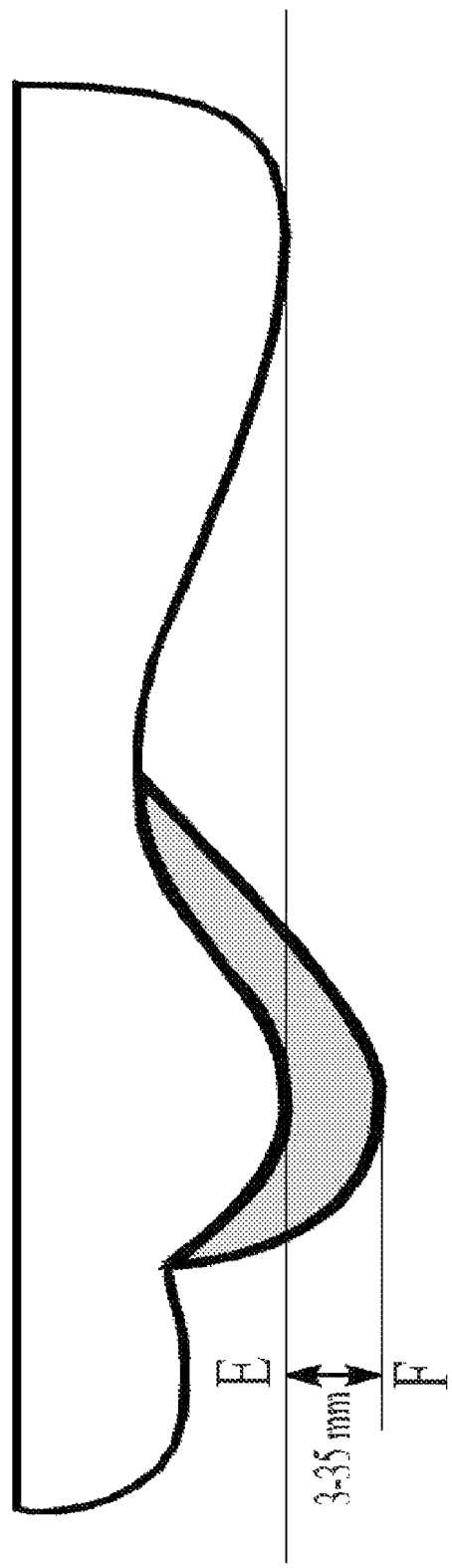
FIG. 7 represents the plaster casting of the foot, with extra space for the metatarsal heads.

FIG. 7 portrays the innovation proposed in this application. As shown, matter has been added to the casting of the insole in the area of the five metatarsal heads of the forefoot. This matter, or insert, creates a distance of between 3 mm and 35 mm between the foot and the insole, as per the requirements of each patient. Distance E-F, described in FIG. 7, represents the thickness of the insert.

Figure 8:
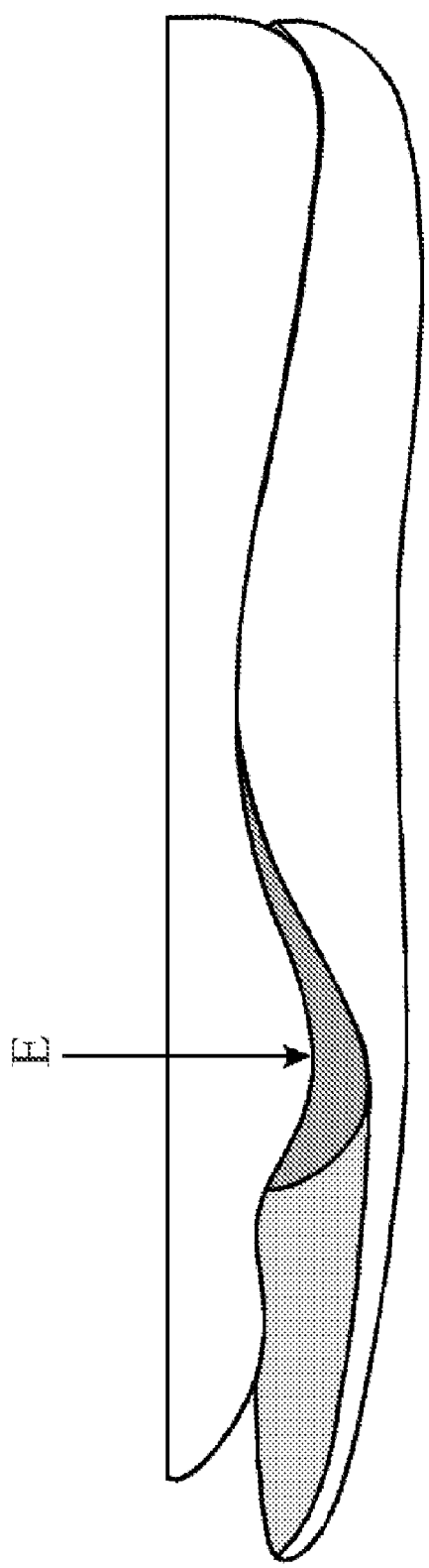
FIG. 8 portrays a model of a foot seated on the new orthopedic insole, which has been equipped with the specially created insert.
Figure 9:
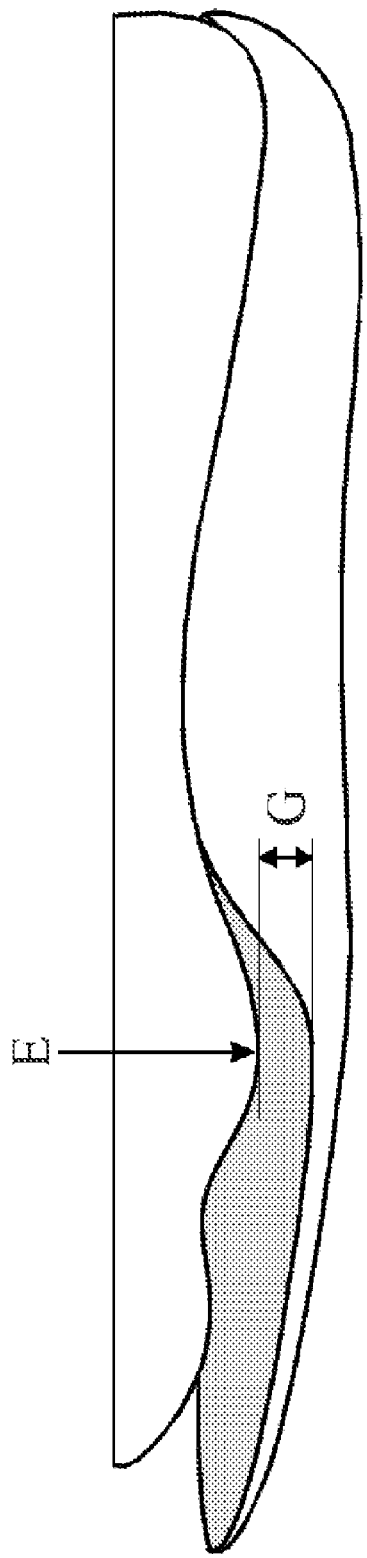
FIG. 9 demonstrates how the foot sits in the new orthopedic insole.

In the final step, the plaster casting and the added insert are used to form the specialized insole. FIG. 8 portrays the creation of the orthopedic insole from the casting with the added insert. FIG. 9 portrays the orthopedic insole and the foot, represented by a plaster model.

The foot now has ample room to take a full step while greatly decreasing angle DD at the area of the five metatarsal heads of the forefoot, significantly reducing the risk of stretching and cracking the skin. The heel will reach the necessary height with minimal bending the foot in the area of the five metatarsal heads of the forefoot. Distance G in FIG. 9 represents the extra space now available for completing a step, ensuring that the foot will not contact the insole in the area of the five metatarsal heads of the forefoot.

Figure 1:
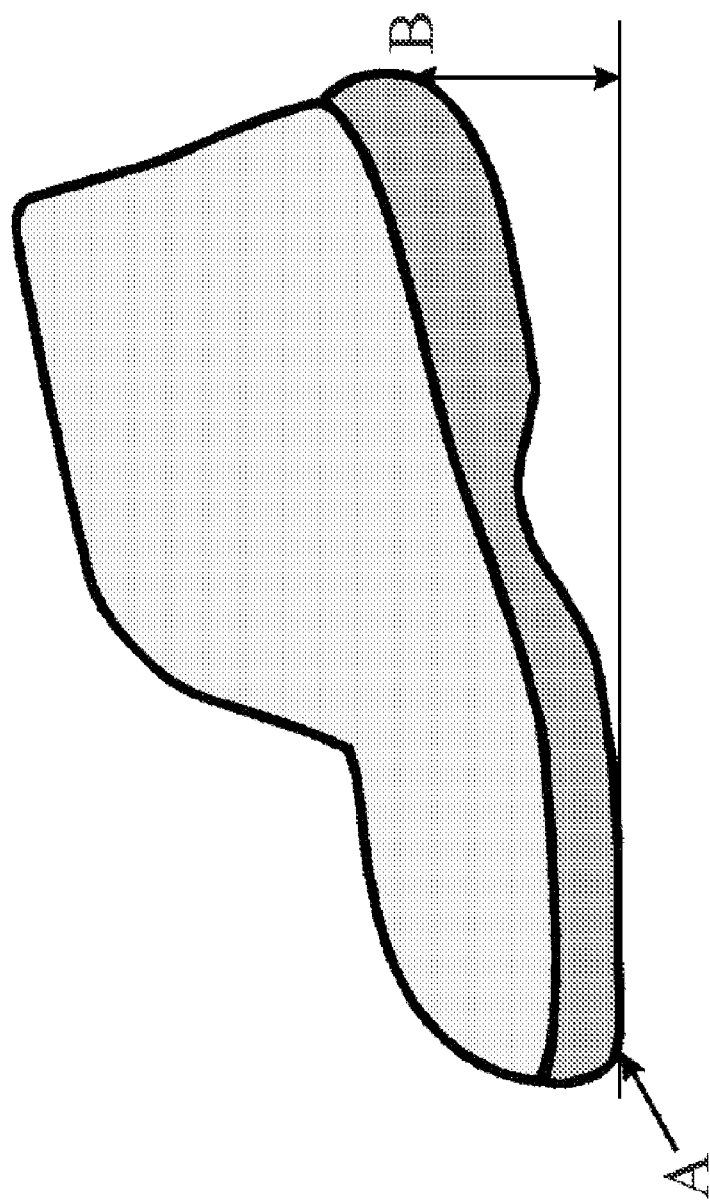
FIG. 1 shows foot placement during the initial phase of the step.
Figure 2:
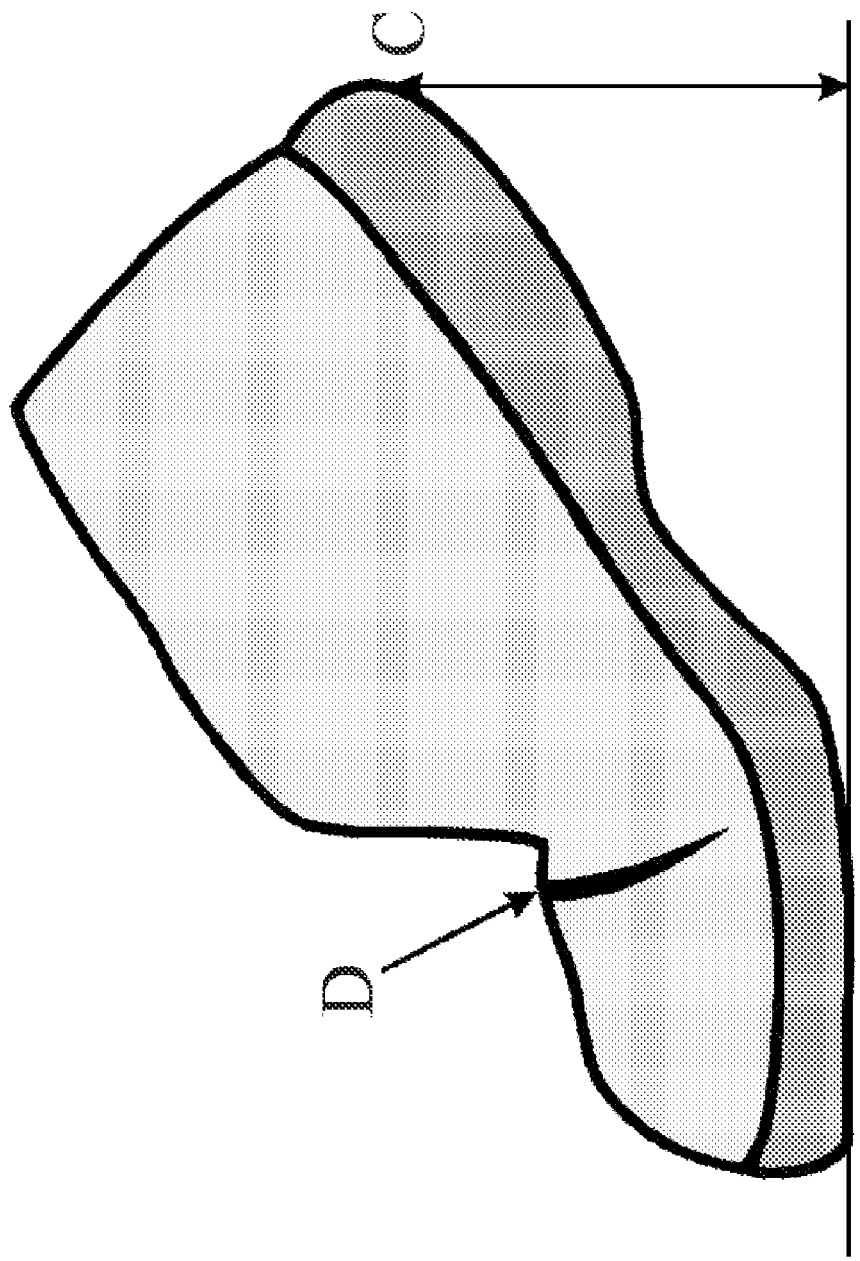
FIG. 2 shows the crease in the shoe caused when the heel reaches maximum height at the final phase of the step.

There is also the option to manufacture the specially equipped insoles in sizes that correspond to standard shoe sizes. In this variation, insoles will be manufactured to fit each shoe size, with different options to be available in each size. When manufacturing such insoles the cast is created in accordance with standard shoes sizes Application When the orthopedic insole, created with the proposed insert, is utilized in shoes, the user will begin taking a step at the heel, as before. The foot will rotate forward until the point where the front of the shoe's sole touches the ground, as seen previously in FIGS. 1 and 2. At this point, the heel will have reached the height necessary to complete the step and the next foot will begin its step. The insole, created by the method described above and equipped with the innovative insert, provides ample room in the area of the five metatarsal heads of the forefoot, allowing the forefoot to lower itself without coming in contact with the insole in this area. The extra room provided by the insert is represented in FIG. 9 by point G. Allowing the heel to reach the height necessary to complete the step, while also decreasing angle DD in the area of the five metatarsal heads of the forefoot, significantly reduces the risk of damaging the skin.

Figure 10:
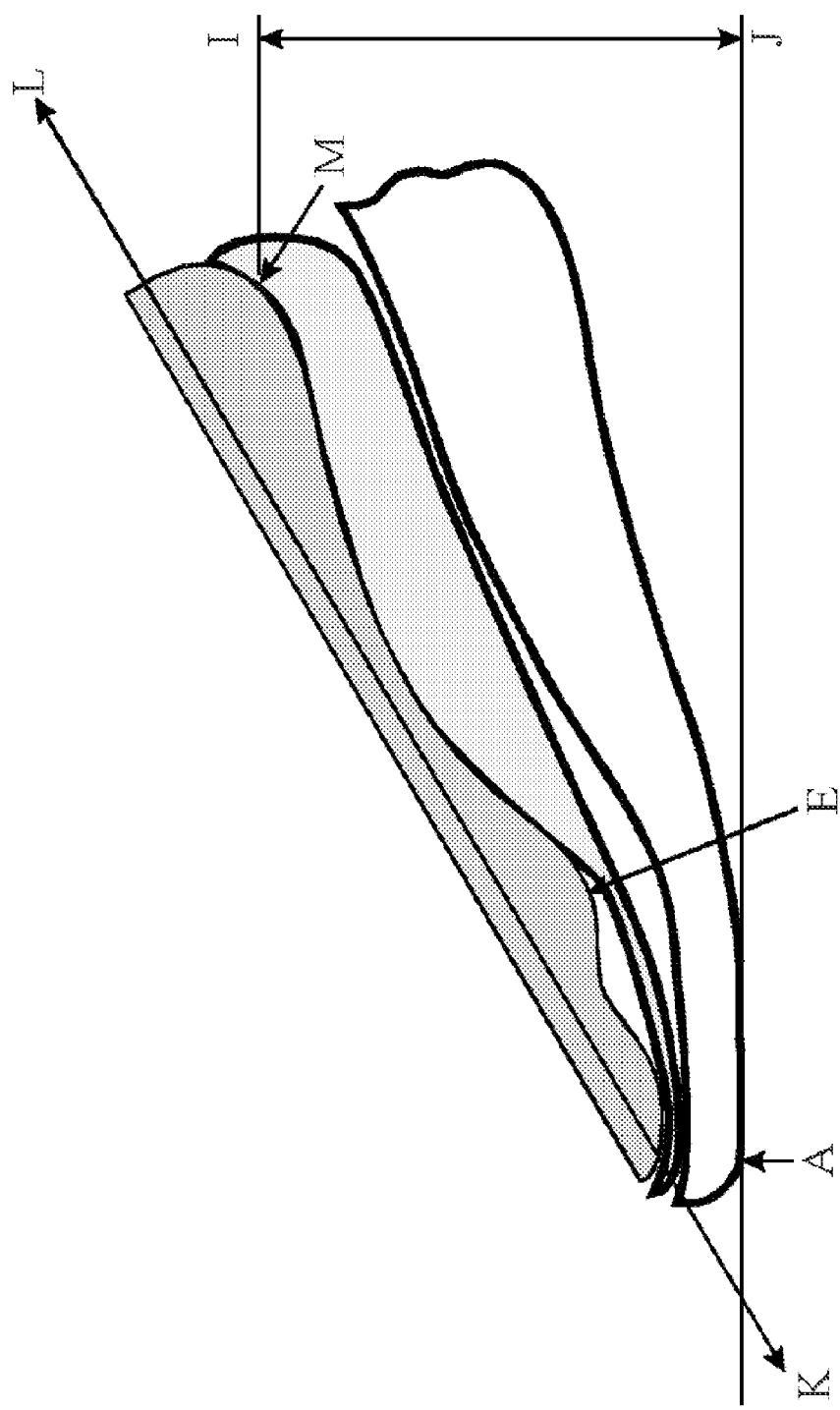
FIG. 10 shows the position of the foot when taking a step, where the present invention is seated on the sole of a shoe.

FIG. 10 portrays a model of a foot, on the specially created orthopedic insole and the sole of a shoe. Point M represents the height that the heel reaches, also represented by the line I-J. Point A shows that the step is completed when the user's toes reach the ground, with significantly reduced bending of the foot at the area of the five metatarsal heads of the forefoot. As can be seen from line K-L, the foot remains relatively straight throughout the entire process of taking a step. Point E shows the metatarsal head, with minimal bending. Because angle DD has been greatly decreased, the risk of skin damage is now significantly reduced.

What is claimed is:

1. A method for creating an adapted insole for preventing skin stretching of a foot at a metatarsal heads area, said method comprised of:
    creating a positive cast of the foot;
    creating a specially designed insert on the positive cast, wherein said insert creates a space in the five metatarsal heads area of a forefoot, thus creating enough space for the foot to complete a step with significantly reduced bending and reduced pressure of the five metatarsal heads area of the forefoot during gait, resulting in prevention of skin stretching at the metatarsal heads area of the foot; and
    creating an orthopedic insole from the cast, wherein said orthopedic insole is molded on the specially designed insert.

2. The method of claim 1 wherein the specially designed insert has a size between 3 mm and 35 mm.

3. The method of claim 1 wherein said orthopedic insole is adapted to fit a personal foot structure of an individual person based on a special cast made from the individual person.

4. The method of claim 1 wherein said orthopedic insole is adapted to fit a given one of a plurality of standard shoe sizes, said specially designed insert having a given size selected from a plurality of sizes available in each of said standard shoe sizes.

* * * * *